(12) United States Patent
Jalaguier et al.

(10) Patent No.: US 10,002,769 B2
(45) Date of Patent: Jun. 19, 2018

(54) METHOD FOR FUNCTIONALIZING A SOLID SUBSTRATE, OTHER THAN A SUBSTRATE MADE OF GOLD, VIA SPECIFIC CHEMICAL COMPOUNDS

(71) Applicant: COMMISSARIAT A L'ENERGIE ATOMIQUE ET AUX ENERGIES ALTERNATIVES, Paris (FR)

(72) Inventors: Eric Jalaguier, Saint Martin D'uriage (FR); Julien Buckley, Grenoble (FR); Xavier Chevalier, Grenoble (FR); Guy Royal, Cruet (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 513 days.

(21) Appl. No.: 14/349,853

(22) PCT Filed: Oct. 5, 2012

(86) PCT No.: PCT/EP2012/069689
§ 371 (c)(1),
(2) Date: Apr. 4, 2014

(87) PCT Pub. No.: WO2013/050512
PCT Pub. Date: Apr. 11, 2013

(65) Prior Publication Data
US 2014/0295213 A1     Oct. 2, 2014

(30) Foreign Application Priority Data
Oct. 6, 2011 (FR) ...................... 11 59045

(51) Int. Cl.
*C25D 9/02* (2006.01)
*C25D 9/04* (2006.01)
(Continued)

(52) U.S. Cl.
CPC ............ *H01L 21/288* (2013.01); *B05D 1/185* (2013.01); *B05D 3/14* (2013.01); *B82Y 30/00* (2013.01);
(Continued)

(58) Field of Classification Search
CPC .............................. H01L 21/244; B05D 1/185
See application file for complete search history.

(56) References Cited

U.S. PATENT DOCUMENTS 5,665,492 A * 9/1997 Sotomura ............. H01M 4/137
427/58
7,927,888 B2    4/2011 Buckley et al.
(Continued)

FOREIGN PATENT DOCUMENTS

EP    1 215 205    6/2002
EP    1 703 572    9/2006
(Continued)

OTHER PUBLICATIONS

Anand, T. J. S., "Synthesis and Characterization of MoS2 Films for Photoelectrochemical Cells", Sains Malaysiana, 38(1)(2009), p. 85-89.*
(Continued)

*Primary Examiner* — Brian W Cohen
(74) *Attorney, Agent, or Firm* — Oblon, McClelland, Maier & Neustadt, L.L.P.

(57) ABSTRACT

The invention relates to a method for functionalizing an electrically conductive substrate, which is not a substrate made of gold, via a layer of chemical compounds, said method comprising the following steps:
- a step in which the electrically conductive substrate is placed in contact with chemical compounds comprising at least a disulfide terminal group;
- a step in which the disulfide terminal group of said chemical compounds is electro-oxidized, causing said (Continued)

chemical compounds to form a layer at the surface of the electrically conductive substrate.

14 Claims, 1 Drawing Sheet

(51) Int. Cl.
| | |
|---|---|
| *C25D 13/02* | (2006.01) |
| *C25D 13/04* | (2006.01) |
| *H01L 21/288* | (2006.01) |
| *B05D 3/14* | (2006.01) |
| *B05D 1/18* | (2006.01) |
| *G11B 9/08* | (2006.01) |
| *C07D 339/04* | (2006.01) |
| *C07D 409/12* | (2006.01) |
| *H01L 21/24* | (2006.01) |
| *H01L 29/40* | (2006.01) |
| *H01L 29/45* | (2006.01) |
| *B82Y 30/00* | (2011.01) |
| *B82Y 40/00* | (2011.01) |

(52) U.S. Cl.
CPC ............ *B82Y 40/00* (2013.01); *C07D 339/04* (2013.01); *C07D 409/12* (2013.01); *C25D 9/02* (2013.01); *C25D 9/04* (2013.01); *C25D 13/02* (2013.01); *C25D 13/04* (2013.01); *G11B 9/08* (2013.01); *H01L 21/244* (2013.01); *H01L 29/401* (2013.01); *H01L 29/45* (2013.01); *B05D 2203/30* (2013.01)

(56) References Cited

U.S. PATENT DOCUMENTS

| | | | |
|---|---|---|---|
| 2002/0127756 A1 | 9/2002 | Wessels et al. | |
| 2004/0137148 A1 | 7/2004 | Lee et al. | |
| 2006/0092687 A1* | 5/2006 | Kuhr .................. | B82Y 10/00 365/151 |
| 2006/0113530 A1 | 6/2006 | Wessels et al. | |
| 2006/0138408 A1 | 6/2006 | Wessels et al. | |
| 2006/0208252 A1 | 9/2006 | Wessels et al. | |
| 2009/0253149 A1* | 10/2009 | Ahrens ................. | C12Q 1/003 435/7.4 |
| 2010/0291303 A1* | 11/2010 | Abys .................... | C23C 18/54 427/343 |
| 2012/0205605 A1 | 8/2012 | Buckley et al. | |

FOREIGN PATENT DOCUMENTS

| | | | | |
|---|---|---|---|---|
| WO | 02 071151 | | 9/2002 | |
| WO | WO 2010066812 A1 * | | 6/2010 | ......... G11C 13/0009 |

OTHER PUBLICATIONS

Harrowfield, J. M., et al., "Cages on Surfaces: Thiol Functionalisation of CoIII Sarcophagine Complexes", Eur. J. Inorg. Chem. 2007, 263-278.*
Oshio, H., Structures and Magnetic Properties of [M(cyclam)(CH3CN)2][Ni(dmit)2]2 (M=Cu, Ni) and [Cu(cyclam)]2[2,5-DM-DCNQI]5, Inorg. Chem. 1993, 32, 4123-4130.*
Matsui, E., et al., "Synthesis of cyclic sulfides by nickel(II) complex-catalyzed intramolecular cyclization of thiolates", Denki Kagakkai Gijutsu, 2008, 15(1), 23-26.*
Mei, et al "Effects of Ligand Coordination Number and Surface Curvature on the Stability of Gold Nanoparticles in Aqueous Solution" Langmuir, 2009, p. 10604-10611.*
Ma et al "Potential-Assisted Deposition of Alkanethiols on Au: Controlled Preparation of Single- and Mixed-Component SAMs" Langmuir, 2000, p. 6188-6190.*
Gropeanu, et al "Synthesis, Stereochemistry and Adsorption Studies of New Spiranes and Polyspiranes Containing 1,2-Dithiolane Units" J. Heterocyclic Chem. 2007, p. 521-527.*
Paik et al "Electrochemical Reactions in Adsorption of Organosulfur Molecules on Gold and Silver Potential Dependent Adsorption" Langmuir, 2000, p. 10198-10205.*
Ulman, A. "Formation and Structure of Self-Assembled Monolayers" Chem. Rev., vol. 96, No. 4, pp. 1533-1554, 1996 XP 002239617.
Lon, A. P. et al. "Gold and Silver Nanoparticles Functionalized by the Adsorption of Dialkyl Disulfides" Langmuir, American Chemical Society, vol. 14, No. 26, pp. 7378-7386, 1998 XP 055030888.
Larsson, M. L. et al. "Direct observation of a self-assembled monolayer of heptyl xanthate at the germanium/water interface: a polarized FTIR study" Journal of Colloid and Interface Science, vol. 273, pp. 345-349, 2004 XP 027132605.
International Search Report dated Jan. 31, 2013 in PCT/EP12/069689 Filed Oct. 5, 2012.
French Search Report dated Jun. 25, 2012 in French Patent Application No. 11 59045 Filed Oct. 6, 2011.

* cited by examiner

METHOD FOR FUNCTIONALIZING A SOLID SUBSTRATE, OTHER THAN A SUBSTRATE MADE OF GOLD, VIA SPECIFIC CHEMICAL COMPOUNDS

TECHNICAL FIELD

The present invention relates to a method for preparing a substrate, other than a substrate made of gold, functionalized by a layer constituted of chemical compounds, said substrates thereby prepared being able to enter into the constitution of memory devices and in particular silicon based memory devices, particularly when the chemical compounds comprise at least a charge storage group.

One of the application areas of the invention is thus that of memory devices using chemical compounds as charge storage compounds (said compounds also being able to be qualified as molecular memories).

STATE OF THE PRIOR ART

Memory devices using molecular memories are based on the principle of the storage of charges at the level of one or more chemical compounds forming coordination complexes with one or more metal elements (said complexes constituting, as such, molecular memories). In order to be able to store one or more charges, said metal complexes must have well defined redox properties and exist in at least two separate oxidation states, which oxidation states correspond to two charge states, one of said states being the "erased" state and the other state being the "written" state. The passage from one state to the other takes place by charge transfer via a reversible oxido-reduction reaction mechanism, under the effect of an external stimulus being able to be of chemical (pH, reagent), photochemical (such as an irradiation at a given wavelength) or electrochemical nature (such as the application of a given oxido-reduction potential, said potential extending conventionally from +2 to −2V). These charge storage memory devices have advantages, such as the reduction in size of the device and the use of low supply voltages. Furthermore, the use of complexes having more than two redox states can make it possible to elaborate multi-bit memory devices.

Nevertheless, to assure all of these functionalities, the aforementioned metal complexes have to be fixed, in a stable manner, on a solid substrate, conventionally electricity conducting, which often implies functionalizing in an appropriate manner said complexes and/or applying a specific surface treatment to the substrate, in order to be able to fix said complexes to the substrate by means of chemical bonds, the fixation of said complexes on a substrate must not affect the switching properties thereof after fixation.

Thus, as an example, the functionalization of metal substrates has been carried out by cyclame compounds using fixation groups of the pyrrole type, with nevertheless, according to this embodiment, the drawback of causing a functionalization in the form of more or less organized multilayers, which adversely affects the uniformity of the properties of the substrate thereby functionalized.

The functionalization of metal substrates made of gold has also been carried out by cyclame compounds complexed with metal copper bearing fixation groups of the thiol type, said functionalization consisting uniquely in soaking the substrate made of gold in a solution comprising said compounds, said compounds organize themselves spontaneously in the form of self-assembled layers on the substrate made of gold, with as major drawback the nature of the substrate.

In fact, gold constitutes a metal contaminant for memory devices incorporating silicon, which makes its use totally unacceptable in this context.

The inventors of the present invention, with regard to the aforementioned problems, set themselves the objective of proposing a novel method for functionalizing electrically conductive substrates by chemical compounds, said substrates being able to be intended to be used in memory devices, not involving the use of gold for the constitution of the substrate and having the following advantages:
   the organization of the chemical compounds in the form of layers at the surface of the substrate, which induces a uniformity of properties of the substrate thereby functionalized; and
   when said chemical compounds are metal complexes, the conservation of the switching properties of said complexes after fixation on the substrate.

DESCRIPTION OF THE INVENTION

The inventors have thus discovered, in a surprising manner, that by using compounds comprising a specific group able after electro-oxidation to fix themselves spontaneously to the surface of an electrically conductive substrate, which does not comprise gold, it is possible to overcome the aforementioned drawbacks and in particular to functionalize such a substrate not comprising gold via a layer of said chemical compounds.

The invention thus relates to a method for functionalizing an electrically conductive substrate, which is not a substrate made of gold, via a layer of chemical compounds, comprising the following steps:
   a step in which the electrically conductive substrate is placed in contact with chemical compounds comprising at least a disulfide terminal group;
   a step in which the disulfide terminal group of said chemical compounds is electro-oxidized, causing said chemical compounds to form a layer at the surface of the electrically conductive substrate.

Functionalization is taken to mean a method of elaborating a layer of molecules of aforementioned chemical compounds at the surface of an electrically conductive substrate.

In particular, said chemical compounds, apart from the presence of at least a disulfide terminal group, may comprise at least a charge storage group, said charge storage group and said disulfide terminal group being potentially separated by at least an organic spacer group, said compounds being able to meet the following generic formula (I):

$$X\text{---}[L\text{---}Z]_n \qquad (I)$$

in which:
   X represents a charge storage group;
   L represents a single bond or an organic spacer group;
   Z represents a disulfide group; and
   n is a whole number ranging from 1 to 6.

The charge storage group may be conventionally an organic group complexing at least a metal element having at least two degrees of oxidation, whereby it constitutes a coordination complex with the or said metal element(s).

Such a coordination complex is thus materialised by a chemical compound comprising functions establishing bonds known as "coordination bonds" with a metal element, said functions comprising conventionally a free doublet, which is going to occupy an empty orbital of the metal element in question.

Such charge storage groups may be, advantageously, polyazacycloalkane groups, i.e., in other words, cycloalkane groups comprising in their ring several nitrogen atoms, a specific example of such groups being able to be a tetraazacycloalkane group, said groups being complexed to at least a metal element.

Tetraazacycloalkane groups according to the invention may meet one of the following formulas (II) to (IV):

(II)

(III)

(IV)

in which:
R$^1$, R$^2$, R$^3$ and R$^4$ represent, independently of each other, an alkyl, aryl, alkylaryl group, a halogen atom, a (alkyl)metallocene group, said groups being able to be perfluorinated;
M is a metal element having at least two degrees of oxidation,
the braces indicating the spot via which these groups are bound to the aforementioned disulfide group via potentially an organic spacer group.

Alkyl group is conventionally taken to mean, in the foregoing and hereafter, a linear or branched alkyl group which can comprise from 1 to 20 carbon atoms or cyclic group, being able to comprise from 3 to 20 carbon atoms. As an example, methyl, ethyl, n-propyl, i-propyl, n-butyl, n-dodecanyl, i-butyl, t-butyl, cyclopropyl, cyclohexyl groups may be cited.

Aryl group is generally taken to mean, in the foregoing and hereafter, an aryl group being able to comprise from 6 to 20 carbon atoms. As examples, benzyl, naphthyl, biphenyl groups may be cited.

Alkylaryl group is generally taken to mean, in the foregoing and hereafter, an aryl group of same definition as that given above, said group being substituted by at least an alkyl group of definition identical to that given above.

(Alkyl)metallocene group is taken to mean a group comprising at least a metal atom sandwiched between at least two conjugated cyclic organic structures, said metallocene group being able to be bound to the cyclame via an alkylene group, in which case one refers to alkylferrocene group.

Perfluorinated is taken to mean a group in which all of the hydrogen atoms are substituted by fluorine atoms.

In particular, when the tetraazacycloalkane groups belong to the category of aforementioned groups of formula (II):
R$^1$, R$^2$, R$^3$ may represent an alkyl group as defined above, a tetraazacycloalkane responding to this specificity being that responding to the following formula (V):

(V)

in which M corresponds to the same definition as that given above; or
R$^1$ may represent an alkyl group and R$^2$ and R$^3$ may represent an (alkyl)metallocene group (symbolised hereafter-CH$_2$-T), a tetraazacycloalkane group responding to this specificity being that meeting the following formula (VI):

(VI)

T representing a ferrocene group, namely two cyclopentadiene groups sandwiching an iron atom.

The aforementioned metal element(s) M may be transition metal elements, such as Cr, Mn, Fe, Co, Ni, Cu.

More particularly, the metal element may be copper, particularly copper, for example, at the degree of oxidation +I or +II.

Tetraazacycloalkane groups, as defined above, are particularly advantageous as charge storage groups, particularly when they complex copper and are so for the following reasons:
they have two discrete redox states (+I and +II), each of said two states having a very high stability;
they exhibit an electrochemical behaviour showing the presence of a hysteresis phenomenon.

Concerning the first aforementioned point, without being linked by theory, the stability results from the fact that the modification of the charge of the metal complex by oxidation or reduction of the complexed metal element induces a movement at the molecular scale, in other words a change of geometry of the complex. This movement is reversible and is behind the very high stabilisation, both chemical and electrochemical, of the charge injected initially. These groups are thus bistable redox molecules existing in two very stable redox states (one redox state being associated with the state "0" and the other redox state being associated with the state "1"), each of said states having a very high charge retention time, the passage from one form to the other taking place in a reversible and reproducible manner by simple transfer of electrons. It is noted, also, that the states "0" and "1" of these groups are particularly stable in the presence of air, which implies that they may be stored without particular precautions.

Concerning the second aforementioned point, without being linked by theory, the two states "0" and "1" of these groups having very distinct oxido-reduction potential (being able to be designated respectively $E^0{}_{State0}$ and $E^0{}_{State1}$) and, at a given potential comprised between $E^0{}_{State0}$ and $E^0{}_{state1}$, said groups remain in their state "0" or their state "1", depending on whether they have been reduced or oxidized beforehand, the passage from one state to the other requiring the application of an overvoltage.

As mentioned above, the charge storage group (for example, X, in the formula (I)) and the disulfide group (for example, Z, in the formula (I)) may be separated by an organic spacer group.

Said organic spacer group may be a hydrocarbon group, being in the form of a linear or branched chain, in which one or more bonding groups can be inserted.

It may be, more particularly, an alkylene group, being able to comprise from 1 to 12 carbon atoms, in which one or more bonding groups can be inserted.

These bonding groups may be —(C=O)—, —(C=O)O—, —SO$_2$ groups, amide groups.

A specific example of alkylene group may be a group of following formula (VII):

The disulfide group according to the invention (which may be in racemic form or in a pure enantiomeric form) may be, preferably, a cyclic disulfide group (which signifies, in other words, that the —S—S— group is incorporated in a ring), being able to meet the following formula (VIII):

the brace indicating the spot via which the disulfide group is bound to the charge storage group via potentially an organic spacer group.

Organic compounds according to the invention may correspond to compounds of following formulas (IX) and (X):

with T being as defined above.

As mentioned above, the substrate intended to be functionalized is an electrically conductive substrate, which is not a substrate made of gold, said substrate being able to be a substrate made of a material selected from carbon, a noble metal such as platinum, a metal oxide such as an indium-tin oxide, a nickel oxide, a transition metal such as nickel and, in particular, vitreous carbon.

According to the invention, the substrate is taken to a potential enabling the electro-oxidation of the disulfide group, which spontaneously causes the fixation of a layer of aforementioned compounds to the surface of the substrate.

According to a first embodiment, this step may consist in subjecting the medium comprising the substrate and the aforementioned compound to a cycling implemented in a range of potentials required for the electro-oxidation of the disulfide group.

In other words, this range of potentials is a range of potentials comprising the oxidation potential of the disulfide group (which may be of the order of +0.8 V with respect to $Ag^0/Ag^+$ (10 mmol·L$^{-1}$ in acetonitrile), the repetition of the number of cycles resulting in a reduction of the anodic intensity at the aforementioned oxidation potential, which indicates that the disulfide groups are consumed in an irreversible manner.

According to a second embodiment, this step may consist in subjecting the medium comprising the substrate and the aforementioned compound to a controlled potential able to enable the oxidation of the disulfide group (said potential being able to be of the order of +0.8 V as mentioned above).

This controlled potential may be applied for a time required to obtain a reduction, in all or part, of the anodic intensity at the aforementioned oxidation potential, which indicates that the disulphide groups are consumed, in all or in part, in an irreversible manner, this reduction being able to be determined by cyclic voltamperometry by those skilled in the art.

The authors of the present invention have been able to note, in a surprising manner, that in oxidizing by electro-chemical means the disulfide group of the aforementioned compounds, the latter become fixed spontaneously and in a concomitant manner to the surface of substrates not comprising gold, in the form of at least a layer, which makes them substrates functionalized via a layer of chemical compounds (organic or organometallic), as defined above, said substrates thereby functionalized then being able to be used as substrates with molecular interrupters when the compounds thereby fixed comprise a group able to assure this function of molecular interrupter.

The characteristics of the substrates and organic compounds are identical to those already mentioned within the scope of the description of the above method.

Thus, the invention also relates to a substrate capable of being obtained by the method as defined above.

Such substrates, particularly when they comprise a layer based on chemical compounds comprising at least a charge storage group, may enter advantageously into the constitution of memory cells intended to enter into the constitution of electronic devices, for example, capacitive memory devices.

"Capacitive memory" is taken to mean any structure able to store charges, integrating or not a capacity as such. The invention applies particularly well to flash type capacitive memories, which store charges in a transistor, or of DRAM type, which store charges in a capacity.

Thus, the invention may relate to a capacitive memory cell comprising at least a substrate functionalized according to the invention, which could, for example, be included in a memory matrix architecture known as "DRAM", for Dynamic Random Access Memory.

A conventional DRAM memory cell is constituted of a MOS transistor (semi-conducting metal oxide) of access and a storage capacity, the capacity being able to be constituted of two electrodes separated by an electrolyte, and charge storage molecules encapsulated in the electrolyte and coupled electronically to one of the two electrodes.

Figure 1:
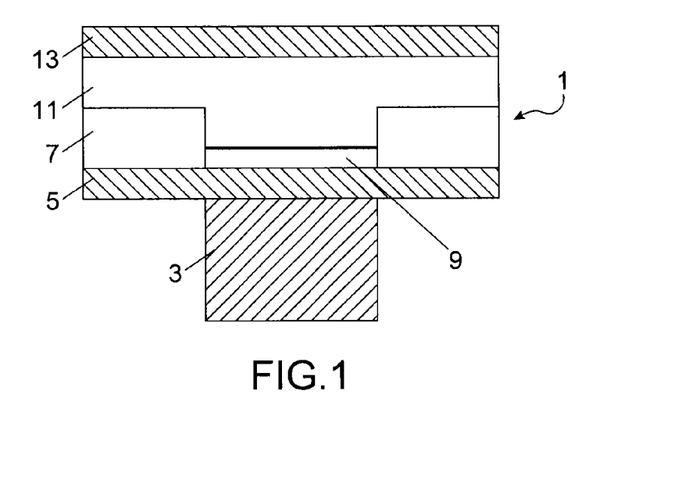
FIG. 1 represents a specific configuration of a capacitive charge storage device according to the invention.

Such a capacity may be in a configuration known as a "stack configuration" as illustrated in appended FIG. 1 (reference 1 in the figure), which comprises:
- a conducting pad 3, which may be made of a metal or metal alloy (for example, W, Al, Cu), made of metal silicide or any other materials used in the electrical interconnections of the Back-End method of CMOS technology of integrated circuits, said pad being able to have a thickness from several hundreds of nanometers (nm) to 1 µm;
- a working electrode 5, for example a metal electrode (such as an electrode made of W, Al, Ti or Cu), a nitride electrode (such as an electrode made of TiN, TaN) or an electrode made of semi-conducting material (such as an electrode made of Si, Ge, SiGe), said electrode being able to have a thickness from several tens of nm to several hundreds of nm;
- an insulating layer 7, such as a layer made of silicon oxide ($SiO_2$) or made of silicon nitride ($Si_3N_4$) deposited to passivate the working electrode 5, said insulating layer being able to have a thickness ranging from several tens of nm to several hundreds of nm;
- a layer of chemical compounds 9 according to the invention, said layer being in contact with the working electrode via its active zone, the whole forming a substrate functionalized according to the invention;
- an electrolytic layer 11, preferably a solid electrolytic layer, for example, an electrolytic gel (such as a gel made of polymethylmethacrylate doped with lithium perchlorate;
- a metal electrode 13 playing the role of reference electrode or counter electrode, by an electrode made of Cu, Ag and/or Pt, said electrode being able to have a thickness ranging from several tens of nm to several hundreds of nm.

The aforementioned electrolytic layer, when it is constituted of an electrolytic gel, may be prepared by dissolution of an electrolyte selected from tetrabutylammonium hexafluorophosphate ($TBAPF_6$), $LiPF_6$, $LiClO_4$ and $LiBF_4$ in a solvent selected from propylene carbonate, sulfolane, 3-methyl-2-oxazolidinone, 4-methyl-2-pentanone. The viscosity of the gel may be controlled by addition of a high molecular weight polymer material selected from poly(vinylidene fluoride)-hexafluoropropylene, 2-hydroxyethyl methacrylate, acrylonitrile, methyl methacrylate, polyethylene oxide, polyphosphazenes.

Alternatively, the electrolytic layer may be replaced by an ionic liquid, the viscosity of which is controlled by a polymer material as described above.

The ionic liquids that are generally used within the scope of the invention are 1-ethyl-3-methyl imidazolium tetrafluoroborate, 1-ethyl-3-methyl imidazolium trifluoromethanesulfonate, 1-(1-butyl)-3-methylimidazolium hexafluorophosphate or 1-butylpyridinium tetrafluoroborate.

The deposition of the electrolytic gel could be carried out by the normal methods used in sol-gel methods: dipping, spin-coating, laminar flow coating, nebulisation (spraying).

Among the organic compounds capable of being used for the implementation of the aforementioned method, certain are new and correspond to organic compounds comprising at least a charge storage group and at least a disulfide terminal group, said charge storage group and said disulfide group being potentially separated by an organic spacer group.

These compounds may meet the following generic formula (I):

in which:
X represents a charge storage group;
L represents a single bond or an organic spacer group;
Z represents a disulfide group; and
n is a whole number ranging from 1 to 6.

The charge storage group may be conventionally an organic group complexing at least a metal element having at least two degrees of oxidation, whereby it constitutes a coordination complex with the or said metal element(s).

Such charge storage groups may be, advantageously, polyazacycloalkane groups, i.e., in other words, cycloalkane groups comprising in their ring several atoms of nitrogen, a specific example of such groups being able to be a tetraazacycloalkane group, said groups being complexed to at least a metal element.

Tetraazacycloalkane groups according to the invention may meet one of the following formulas (II) to (IV):

(IV)

in which:
- $R^1$, $R^2$, $R^3$ and $R^4$ represent independently an alkyl, aryl, alkylaryl groups, a halogen atom, said groups being able to be perfluorinated;
- M is a metal element having at least two degrees of oxidation,
- the braces indicating the spot via which said groups are bound to the disulfide group via potentially an organic spacer group.

In particular, when the tetraazacycloalkane groups belong to the category of aforementioned groups of formula (II):
- $R^1$, $R^2$, $R^3$ may represent an alkyl group as defined above, a tetraazacycloalkane responding to this specificity being that meeting the following formula (V):

(V)

in which M corresponds to the same definition as that given above; or
- $R^1$ may represent an alkyl group and $R^2$ and $R^3$ may represent a (alkyl)metallocene group, a tetraazacycloalkane group responding to this specificity being that meeting the following formula (VI):

(VI)

T representing a ferrocene group, namely two cyclopentadiene groups sandwiching an iron atom.

The metal element(s) mentioned above may be transition metal elements, such as Cr, Mn, Fe, Co, Ni, Cu.

More specifically, the metal element may be copper, and more specifically copper at the degree of oxidation (II).

The advantages of this type of compound mentioned above in the part relative to the description of the method may be reproduced here.

As mentioned above, the charge storage group (for example, X, in the formula (I)) and the disulfide group (for example, Z, in the formula (I)) may be separated by an organic spacer group.

Said organic spacer group may be a hydrocarbon group, being in the form of a linear or branched chain, in which one or more bonding groups can be inserted.

It may be, more particularly, an alkylene group, being able to comprise from 1 to 12 carbon atoms, in which one or more bonding groups can be inserted.

These bonding groups may be —(C=O)—, —(C=O)O—, —SO₂ groups, amide groups.

A specific example of alkylene group may be a group of following formula (VII):

(VII)

The disulfide group according to the invention may be a cyclic disulfide group (which signifies, in other words, that the group —S—S— is incorporated in a ring), being able to meet the following formula (VII):

(VIII)

the brace indicating the spot by which the disulfide group is bound to the charge storage group via potentially a spacer group.

Organic compounds according to the invention may be selected from compounds of following formulas (IX) and (X):

(IX)

(X)

with T being as defined above.

The invention will now be described with reference to the particular embodiment below, given for illustrative purposes and non-limiting.

DETAILED DESCRIPTION OF PARTICULAR EMBODIMENTS

In this part will be illustrated:

the preparation of a specific organic compound comprising a disulfide terminal group (Example 1);

the functionalization of an electrode made of vitreous carbon by this compound and the study of the system obtained by voltammogram (Example 2).

EXAMPLE 1

This example illustrates the preparation of a compound of following formula (XI):

(XI)

which takes place in three steps:

the synthesis of 1,4,8,11-tetraazatricyclo[9,3,1,1]hexadecane of following formula (XII):

(XII)

from the compound of formula (XII), the synthesis of the iodide salt of methyl-4,11-diazoniatricyclo[9,3,1,1] hexadecane of following formula (XIII):

(XIII)

from the compound of formula (XIII), the synthesis of (propan-3-nitrile)-4,8,11-trimethyl-1,4,8,11-tetraazacyclotetradecane of following formula (XIV):

(XIV)

from the compound of formula (XIV), the synthesis of (butan-4-amine)-4,8,11-trimethyl-1,4,8,11-tetraazacyclotetradecane of following formula (XV):

(XV)

from the compound of formula (XV), the synthesis of the compound of formula (XVI) mentioned above.

a) Synthesis of the Compound of Formula (XII)

Two equivalents of formaldehyde (0.9 mL; 37% in water) are added rapidly to an aqueous solution of cyclame (1 g; 1.07 mmoles in 60 mL) at 0° C. The mixture obtained is placed under stirring for 2 hours, whereby a white precipitate forms, which is then filtered, washed with water and dried under reduced pressure. The white powder obtained is used without purification.

The yield is 96%.

The $^1$H NMR and $^{13}$C NMR results confirm the compound of formula (XII) is obtained.

b) Synthesis of the Compound of Formula (XIII)

600 mg of the compound of formula (XII) are dissolved in 70 mL of dry diethyl ether. After 20 minutes of bubbling under argon, 10 mL of a solution of diethyl ether containing 75 μL of iodomethane (2.8 mmoles; 1.05 equivalents) is added slowly. After 24 hours under vigorous stirring in darkness, a white precipitate forms, which is then filtered and washed with 2*40 mL of diethyl ether. The white powder obtained is then dissolved in 100 mL of chloroform, the solution being filtered to eliminate impurities. The solution is evaporated under vacuum, leaving a colourless oil remaining, which crystallizes slowly in the form of white platelets. The yield is 85%.

The $^{13}$C NMR results confirm the compound of formula (XIII) is obtained.

c) Synthesis of the Compound of Formula (XIV)

To a solution of acetonitrile comprising the compound of formula (XIII) (1.47 g; 4 mmoles in 30 mL) is added rapidly an excess of iodobutyronitrile (1.48 g; 7.6 mmoles). The solution obtained is degassed by bubbling with argon and heated to 70° C. for 30 minutes. The temperature is then maintained at 50° C. for 3 days.

A white precipitate is obtained corresponding to a bis-ammonium salt of following formula (XIV'):

(XIV')

This precipitate is filtered, washed with 2*50 mL of acetonitrile, 50 mL of dichloromethane and 100 mL of diethyl ether and the resulting white powder is dried under reduced pressure (1.43 g).

Starting from the aforementioned compound, the compound of formula (XIV) is obtained in the following manner.

To a methanolic solution of the compound of formula (XIV') under magnetic stirring, is added an excess of sodium borohydride. The resulting mixture is left to react for several hours. The solution is then concentrated under reduced pressure and 50 mL of distilled water are added. The aqueous solution is then extracted with 3*50 mL of chloroform. The organic phases are combined, dried over $MgSO_4$, evaporated and dried under reduced pressure, whereby a colourless oily residue is obtained.

The $^1H$ NMR and $^{13}C$ NMR results confirm the compound of formula (XIV) is obtained.

d) Synthesis of the Compound of Formula (XV)

To an ethanolic solution of compound of formula (XIV) under stirring (0.3 g; 0.97 mmoles in 60 mL), is added rapidly sodium hydroxide (90 mg; 2.21 mmoles). To this mixture under stirring is added, alternatively and by small fractions, hydrazine monohydrate (700 µL; 13 mmoles; 15-20 equivalents) and Raney nickel in ethanol (0.4 g in 10 mL). The mixture is left to react for 24 hours then filtered on a Millipore filter. The filtrate is evaporated and the residue is dissolved in a minimal volume of toluene. The solution is filtered to eliminate the excess of sodium hydroxide. The filtrate is evaporated and dried under reduced pressure, whereby a colourless oily residue (Yield: 0.279 g; 92%) is obtained.

The $^1H$ NMR and $^{13}C$ NMR results confirm the compound of formula (XV) is obtained.

e) Synthesis of the Compound of Formula (XI)

To a solution under stirring comprising anhydrous dichloromethane and D,L-lipoic acid (200 mg; 0.96 mmoles in 30 mL), degassed beforehand with argon and cooled to 0° C., is added a solution of (2-(1H-7-azabenzotriazol-1-yl)-1,1,3,3-tetramethyluronium hexafluorophosphate methanaminium (0.366 g; 0.96 mmoles) dissolved in 2 mL of anhydrous dimethylformamide. Distilled triethylamine (400 µL; 2.88 mmoles) is then added and the mixture is stirred for 15 minutes at ambient temperature. The solution is cooled to 0° C. and a solution comprising anhydrous dichloromethane and the compound of formula (XV) (278 mg; 0.886 mmoles in 35 mL) is added drop by drop. The mixture obtained is then left under stirring at ambient temperature for 24 hours. The solvents are evaporated under reduced pressure and the oily residue obtained is purified by column chromatography (neutral alumina, deactivated with an ethyl acetate/water/methanol (150/1/20) mixture) with pure ethyl acetate as starting elution solvent then increasing quantities of methanol (5-20%) during the elution. The main fraction is evaporated up to dryness and the colourless oily residue obtained is dried under reduced pressure (Yield: 0.365 g; 82%).

The $^{13}C$ NMR results confirm the compound of formula (XI) is obtained.

EXAMPLE 2

In this example is illustrated the functionalization of a vitreous carbon electrode.

Prior to this functionalization, the preparation is carried out of a copper complex of formula (IX) defined above obtained from the compound prepared according to example 1 in the manner described below.

To a solution of the compound (XI) (50 mg; $9.97*10^{-5}$ moles) dissolved in 15 mL of methanol are added, under stirring and at ambient temperature, 32.6 mg of Cu $(BF_4)_2.6H_2O$ ($9.47*10^{-5}$ moles; 0.95 equivalents) dissolved beforehand in 5 mL of methanol. After 30 minutes of stirring, the solvent is evaporated under reduced pressure then the evaporation residue is washed with 2*10 mL of cold methanol then 50 mL of diethyl ether. The residue is then again dissolved in 5 mL of acetonitrile then precipitated by addition of 30 mL of diethyl ether and filtered. A hygroscopic blue powder is obtained and is dried under vacuum. The complex is obtained with a yield of around 80%.

To functionalize the vitreous carbon electrode, it is immersed in a solution comprising the copper complex of formula (IX), the preparation method of which is described above, said complex being present at a concentration of 1 mM in acetonitrile, and is then subjected to a step of cycling between −0.2 to +1 V/Ag—$Ag^+$ ($10^{-2}$ M in acetonitrile) at a scanning speed of 100 $mV·s^{-1}$, the number of cycles carried out being 5.

The electrochemical assembly used is an assembly with three electrodes with an organic electrolyte comprising:
  a reference electrode consisting of a solid silver wire placed in contact with a solution of $AgNO_3$ ($10^{-2}$ M) in acetonitrile;
  a working electrode consisting of a vitreous carbon disc of 3 mm diameter;
  a counter electrode consisting of a platinum wire; and
  an electrolyte consisting of acetonitrile containing tetrabutylammonium perchlorate (0.1 M) and the copper complex of formula (IX) (1 mM).

Following this functionalization and after rinsing with acetonitrile, the electrode thereby modified is subjected to a cyclic voltamperometry experiment consisting in subjecting the substrate thereby coated to successive cycles (150 in number) between −1 V and +0.1 V with respect to $Ag/Ag^+$ ($10^{-2}$ M) at a rate of 50 $V·s^{-1}$.

The assembly used comprises:
  a reference electrode consisting of a solid silver wire placed in contact with a solution of $AgNO_3$ ($10^{-2}$M) in acetonitrile;
  a working electrode consisting of the coated substrate;
  a counter electrode consisting of a platinum wire; and
  an electrolyte consisting of acetonitrile containing tetrabutylammonium perchlorate (0.1 M).

Figure 2:
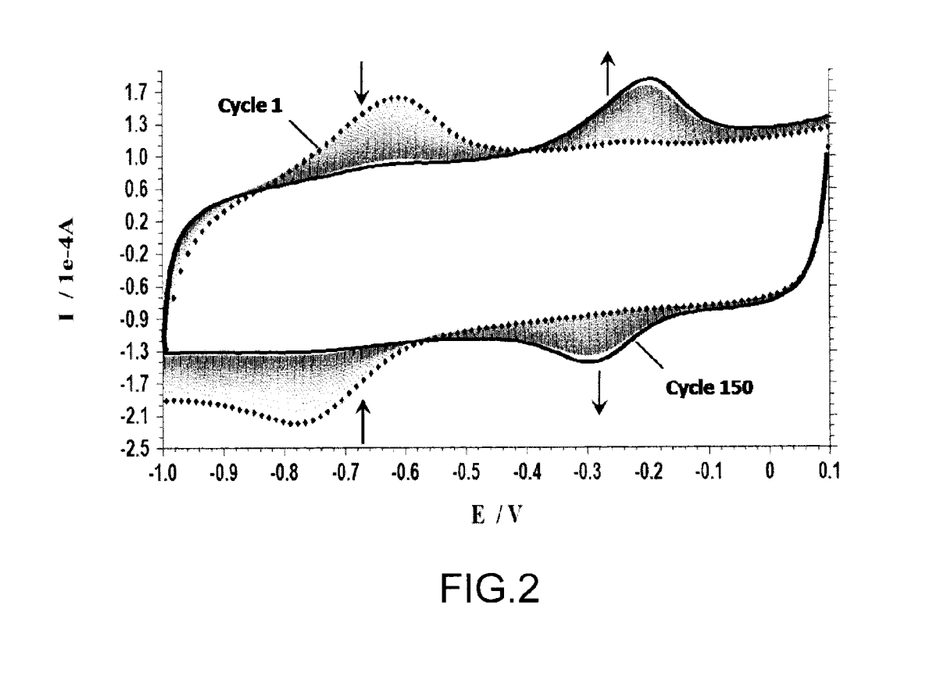
FIG. 2 represents a voltamperogram obtained within the scope of example 2.

The voltammogram obtained is represented in appended FIG. 2.

For the cycle 1 indicated in the figure, a reversible redox system (centred around −0.7 V) may be noted attributed to the redox system of $Cu^{II}$ for the compound grafted in a diastereoisomeric configuration of type I, corresponding to the diastereoisomer RSRS.

As the cycles proceed, this redox system disappears to the benefit of a new reversible redox system (centred around −0.25 V) attributable to the redox system of $Cu^{II}$ for the compound grafted in a diastereoisomeric configuration of type V (corresponding to the diastereoisomer RRRR), as is illustrated for the cycle 150 represented in the same FIG. 2.

This indicates, without ambiguity, that the electron transfer reactions of the complex immobilised on a surface are coupled to chemical reactions and that the passage from one state to the other is realised. The two stable forms of the "switch" have oxido-reduction potentials separated by 500 mV, which attests to a stabilisation of the different redox states.

With a view to storage of information, the fact of being able to identify the two isomers (type I and type V) at a high scanning speed signifies that it is possible to read the corresponding two items of information without too much loss of information. In other words, it is possible to read the information ("0" or "1") without transforming the "0" into "1" and vice versa.

The invention claimed is:

1. A method for functionalizing an electrically conductive substrate via a layer comprising a chemical compound, the substrate being a substrate made of a material selected from the group consisting of carbon, platinum, an indium-tin oxide and nickel, comprising:

contacting the electrically conductive substrate with a chemical compound comprising at least a disulfide terminal group, said chemical compound satisfies formula (I):

(I)

wherein:

X is a charge storage group, which is a polyazacycloalkane group complexed with at least a metal element, said polyazacycloalkane group being a tetraazacycloalkane group selected from the group consisting of formula (II), formula (III) and formula (IV):

(II)

(III)

(IV)

wherein:

$R^1$, $R^2$, $R^3$ and $R^4$ represent, independently of each other, an alkyl, aryl, alkylaryl group, a halogen atom, an (alkyl)metallocene group, wherein the alkyl, aryl, alkylaryl, (alkyl)metallocene group may be perfluorinated;

M is a metal element having at least two degrees of oxidation;

braces indicating the spot through which said tetraazacycloalkane group is bound to the disulfide group via a spacer group;

L is a single bond or an organic spacer group;

Z is a cyclic disulfide group; and n is a whole number ranging from 1 to 6; and electro-oxidizing the cyclic disulfide terminal group of said chemical compounds, causing said chemical compounds to form a layer at the surface of the electrically conductive substrate.

2. The method of claim 1, wherein the tetraazacycloalkane group is of formula (II).

3. The method of claim 1, wherein the tetraazacycloalkane group satisfies one of formula (V) and formula (VI):

(V)

(VI)

wherein: M is a metal element having at least two degrees of oxidation; and

T represents a ferrocene group.

4. The method of claim 1, wherein the metal element is a transition metal element.

5. The method of claim 4, wherein the transition metal element is selected from the group consisting of Cr, Mn, Fe, Co, Ni, and Cu.

6. The method of claim 1, wherein the metal element is copper.

7. The method of claim 1, wherein said charge storage group and said disulfide terminal group are separated by an organic spacer group which is a hydrocarbon group, being in the form of a linear or branched chain, in which one or more bonding groups can be inserted.

8. The method of claim 7, wherein the hydrocarbon group is an alkylene group, in which one or more bonding groups can be inserted.

9. The method of claim 7, wherein the one or more bonding groups are selected from the group consisting of a —(C=O)— group, a —(C=O)O group, a —SO$_2$ group, and an amide group.

10. The method of claim 1, wherein said charge storage group and said disulfide terminal group are separated by an organic spacer group satisfying the following fomula (VII):

—(CH$_2$)$_4$—NH—CO—(CH$_2$)$_4$—      (VII).

11. The method of claim 1, wherein the disulfide group is a group of following formula (VIII):

(VIII)

12. The method of claim 1, wherein the chemical compounds satisfy one of formula (IX) and formula (X):

(IX)

(X)

wherein T represents a ferrocene group.

13. The method of claim 1, wherein the tetraazacycloalkane group is of formula (III).

14. The method of claim 1, wherein the tetraazacycloalkane group is of formula (IV).

* * * * *